United States Patent
Danz et al.

(10) Patent No.: US 6,455,320 B1
(45) Date of Patent: Sep. 24, 2002

(54) SOLAR CELL SENSORS, PROCESS FOR THEIR MANUFACTURE AND THEIR USE

(75) Inventors: Rudi Danz, Kleinmachnow; Burkhard Elling, Potsdam, both of (DE)

(73) Assignee: Fraunhofer-Gesellschaft zur Foerderung der Angewandten Forschung E.V. (DE)

( * ) Notice: Subject to any disclaimer, the term of this patent is extended or adjusted under 35 U.S.C. 154(b) by 0 days.

(21) Appl. No.: 09/626,897

(22) Filed: Jul. 27, 2000

(30) Foreign Application Priority Data

Jul. 27, 1999 (DE) .......................................... 199 35 180

(51) Int. Cl.$^7$ ............................................... G01N 21/64
(52) U.S. Cl. .................. 436/172; 422/82.08; 422/82.09
(58) Field of Search .......................... 422/82.06, 82.07, 422/82.08, 82.09; 250/458.1, 459.1; 436/172, 164, 167, 169

(56) References Cited

U.S. PATENT DOCUMENTS

| | | | | |
|---|---|---|---|---|
| 4,127,738 A | * | 11/1978 | Ghosh et al. | 136/255 |
| 4,629,821 A | * | 12/1986 | Bronstein-Bonte et al. | 136/257 |
| 4,836,012 A | * | 6/1989 | Doty et al. | 73/23 |
| 4,891,075 A | * | 1/1990 | Dakubu | 136/257 |
| 4,957,012 A | * | 9/1990 | Cuddihy et al. | 219/502 |
| 4,968,631 A | * | 11/1990 | Dakubu | 436/111 |
| 5,037,615 A | * | 8/1991 | Kane | 422/82.08 |
| 5,365,068 A | * | 11/1994 | Dickerson | 250/372 |
| 5,591,975 A | * | 1/1997 | Jack et al. | 250/338.5 |
| 5,656,817 A | * | 8/1997 | Bower et al. | 250/370.02 |
| 5,772,328 A | * | 6/1998 | Kronberg | 374/162 |
| 5,866,433 A | | 2/1999 | Schalkhammer et al. | |
| 5,869,972 A | | 2/1999 | Birch et al. | |
| 6,285,807 B1 | * | 9/2001 | Walt et al. | 250/227.14 |

FOREIGN PATENT DOCUMENTS

| | | |
|---|---|---|
| AT | 403 961 B | 7/1998 |
| DE | 36 06 557 A1 | 9/1987 |
| DE | 40 18 053 A1 | 9/1991 |
| DE | 43 32 512 C2 | 3/1995 |
| DE | 197 07 776 A1 | 10/1997 |
| DE | 197 25 050 A1 | 12/1998 |
| JP | 05013794 | * 1/1993 |

OTHER PUBLICATIONS

Miguel Angel Gonzalez–Martinez, Rosa Puchades, Angel Maquieira; "On–line immunoanalysis for environmental pollutants: from batch assays to automated sensors"; Trends in Analytical Chemistry, vol. 18, No. 3; 1999; pp. 204–218.

Sensor System for Environmental Monitoring, vol. Two: Environmental Monitoring; Edited by M. Campbell, Department of Physical Sciences, Glasgow Caledonian University, Glasgow, UK; Blackie Academic & Professional, London, UK, 1997.

* cited by examiner

*Primary Examiner*—Jeffrey Snay
(74) *Attorney, Agent, or Firm*—Marshall & Melhorn, LLC

(57) ABSTRACT

A novel solar cell is shown, along with a method for the manufacture thereof, whereby molecules whose presence are to be verified and/or substances are deposited on such solar cells and are influenced by chemical or physical parameters to cause a change in the original electric parameters of the solar cells, such as photoelectric current or photoelectric voltage which facilitates the detection of chemical, biochemical and/or physical perimeters and substances on the solar cells. The sensitive molecules and/or substances, under certain conditions, also produce color or transmission changes, so that the photoelectric current of the solar cells change and, therefore can also be used as an indicator.

29 Claims, 2 Drawing Sheets

SOLAR CELL SENSORS, PROCESS FOR THEIR MANUFACTURE AND THEIR USE

BACKGROUND OF THE INVENTION

1. Field of the Invention

The present invention relates to mobile sensors and processes for their manufacture and use. Such sensors are used for verifying the presence of gases, liquids or solid substances or for the measurement of physical or chemical parameters such as, for example, pressure, temperature, humidity, pH-value and the like. The areas of application are in medicine, biotechnology, environmental technology or in the general area of measuring technology.

2. Discussion of the Related Art

From the state of the art, various different sensors for verifying the presence of chemical or physical parameters are known (Sensor Systems for Environmental Monitoring, Ed. M. Campbell, Blackie Academic, London 1997). A disadvantage of the sensors known in the state of the art is the high cost associated with the construction of the device and the specialization of certain parameters. Furthermore, such sensors cannot be used as independent devices and require special light sources, for example, laser diodes, and a special voltage supply, which, however, can also be provided by means of solar cells. This, however, limits the mobility of the sensors and increases their manufacturing and operating costs.

It is the objective of the present invention to provide a process for the determination of a quantity to be measured, a sensor as well as a process for the manufacture and application of such sensors, which make possible a mobile and efficient measurement of chemical and/or physical parameters, of gases, liquids and/or solid substances at a low technical expenditure. Furthermore, he sensors are to be manufacturable in a cost-effective and simple manner and the process is be able to be carried out in a simple manner.

SUMMARY OF THE INVENTION

This problem is solved by the process for detecting a quantity to be measured according to claim 1, the sensor according to claim 6, the process for its manufacture according to claim 17 as well as the applications according to claim 20. Advantageous further developments of the processes, sensors and uses according to the invention are provided in the dependent claims.

DESCRIPTION OF THE PREFERRED EMBODIMENTS

Figure 1:
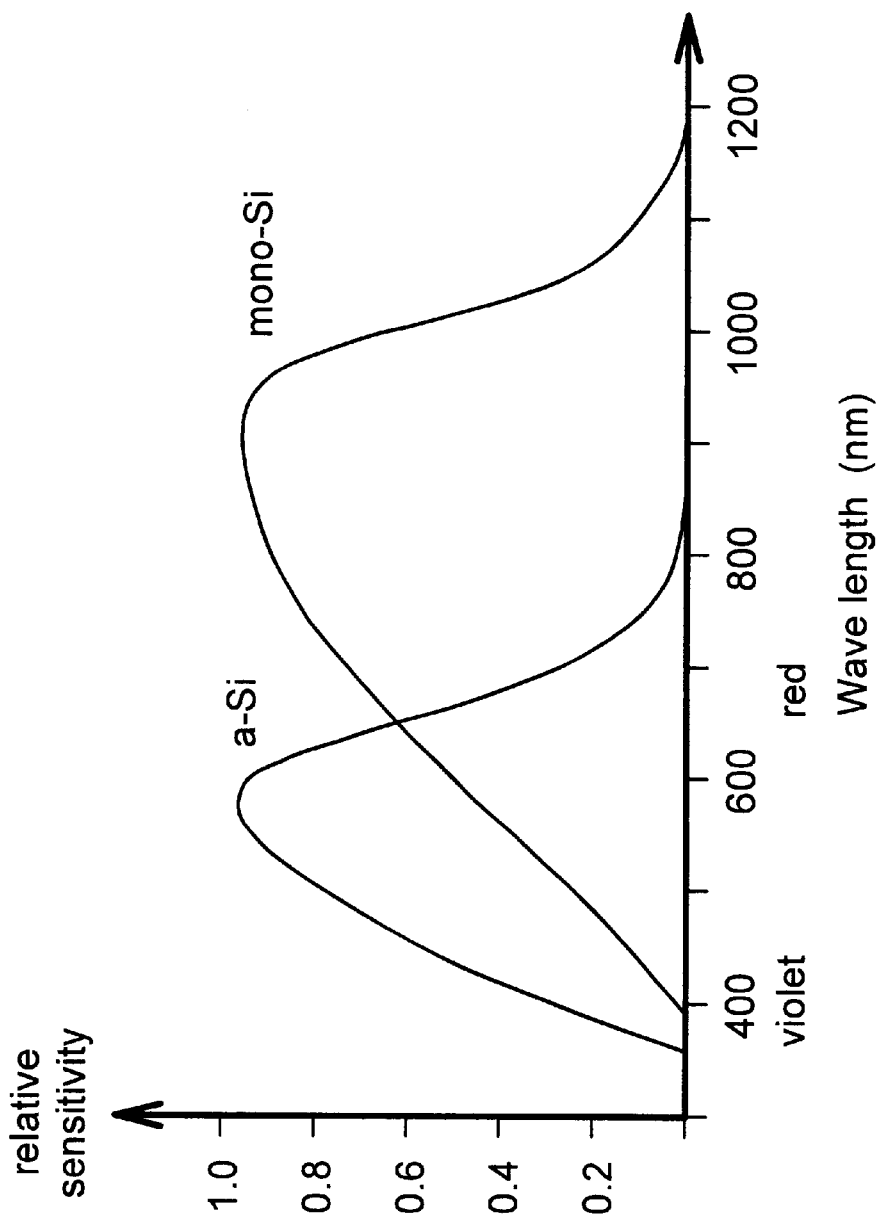
FIG. 1 is a chart showing the relative spectral current sensitivities of amorphous and crystalline silicon solar cells.

According to the invention the problem is solved in that selected sensitive and fluorescent molecules and/or molecules whose presence is to be verified and/or substances are deposited on solar cells, where the sensitive molecules and/or substances—under the influence of solid liquid and/or gaseous substances or under the influence of chemical or physical parameters, such as, for example, pressure, temperature, humidity, pH-value, —change the radiation impinging upon the solar cells—reversibly and selectively—with respect to its spectral distribution and/or intensity. In this manner, a change of the original electrical parameters of the solar cells, such as photoelectric current or photoelectric voltage, is generated, which facilitates the detection of chemical, biochemical and/or physical parameters and substances. The sensitive molecules and/or substances, under certain conditions, also produce color or transmission changes, so that the photoelectric current of the solar cells changes and, therefore, can also be used as an indicator, when the optical properties of the substances deposited are well matched to the spectral current sensitivities of the materials of the solar cells used.

According to the invention the process consists in that either a solar cell is first coated with the sensitive substances, which are effective as indicators, and subsequently the coated solar cell under the impingement of light is exposed to the physical or chemical parameters or the gases, liquids or solid substances, or by mixing the indicators with the gaseous, liquid or solid substances and immediately depositing them on the solar cell.

In the case of suitable substances to be detected these themselves can be used as indicators, so that only the substance to be detected is deposited on the solar cell.

Under the influence of light, the radiation, which penetrates to the solar cell, then changes in its intensity or spectral distribution, which results in a change of the photoelectric current or the photoelectric voltage.

The sensors according to the invention thus consist of a solar cell, which is at least partially coated with indicators, where the indicators are advantageously immobilized in a polymer matrix. Such sensors can be produced by centrifuging, sputtering or vapor deposition of the indicators on the surface of the solar cells. The natural and/or artificial light, which is radiated upon the solar cell, here acts as a measuring ray of light and also, at the same time, for the generation of the electric power in the solar cell for the operation of possibly present evaluation units or the like.

The sensors according to the invention as well as the detection process according to the invention can be used for verifying the presence of gases, liquids or solid substances as well as for verifying the presence of physical or chemical parameters, for example for verifying the presence of oxygen, ammonia, sulphur dioxide, metals such as mercury ions, ozone, for determining the pH-value, pressure, temperature or humidity. Such mobile, independent and cost-effective sensors are used in particular in the areas of medicine, biotechnology, environmental technology or measurement technology.

Suitable for use as solar cells are solar cells which are based on amorphous or crystalline silicon, gallium arsenide compound, indium phosphide compound, germanium, selenium, cadmium telluride, cadmium sulfide, copper indium gallium diselenide, copper-indium-sulfide or mixed compounds of these elements. Suitable polymer coatings are polymer matrices made of siloxanes, polyhydroxyethyl-methacrylatene, ormoceres, polystyrene, cellulose polymers and/or polymers containing starch, acetate polymers, polycarbonates, polyvinyl alcohol, polyacetals, paraloid, polymethyl-methacrylate, polyurethane, alkyd resins, epoxide and melamine resins, polymethyl pentene, polyvinyl chloride or the like. For use as sensitive and fluorescent molecules and/or substances, the kind of materials are suitable, which manifest a strong fluorescence amplification or extinction or change of their spectral transmission, if the molecules and/or substances, which are specifically to be detected, occur at the sensor element according to the invention, or if the temperature, pressure or humidity or other physical or chemical parameters change. For example, for verifying the presence of oxygen, fluorescent porphyrines, chlorophyll, fluoresceines, rhodamines, ruthenium or phthalocyanine complexes, pyrenes or other polycyclic aromatics or special fluorescent substances or rare earths are suitable. If the oxygen concentration is increased, this results in an extinction of the fluorescence of the indicated molecules, which reduces the radiation impinging on the solar cell and thus the photoelectric current. The sensitive substances shown are suitable for pressure measurements because of their sensitivity to oxygen.

For the measurement of temperature, special fluorescent dyes, such as, for example, rhodamines, perylenes, pyronines and the like can be used as indicators. However, temperature measurements can also be made with thermochromic and/or thermotropic substances as indicators. In this case, the spectral transmission of the indicators changes as a function of the temperature and effects a change in the photoelectric current, which serves for indicating the temperature.

In FIG. 1, for example, the relative spectral current sensitivities of amorphous and crystalline silicon solar cells are shown. Because of the spectral current sensitivities, in the case of amorphous silicon, for example, an increase in current results, when the irradiating light is amplified by a fluorescent substance under the influence of a chemical or physical parameter by fluorescence in the spectral range of 500 to 600 nm. Conversely, an extinction of the fluorescence results in a reduction of the photoelectric current. Changes in the color and transmission of the sensitive molecules and substances deposited on the solar cells and/or the molecules and/or the substances whose presence is to be verified also result in changes of the photoelectric current, and, therefore, are also suitable to function as indicators. Similar principles are also valid for crystalline silicon and other solar cell materials. In the case of crystalline silicon a red shift in the impinging radiation always leads to an increase of the photoelectric current, so that the parameters, which, as a result of fluorescence, cause a transformation of the light toward a longer wavelength radiation, can be readily demonstrated.

The indicators are to be matched with the solar cell material in question. Depending on their fluorescent qualities and/or their absorption behavior other solar cell materials can also be used. The above-mentioned solar cell materials show varying electronic energy differences and thus also different spectral sensitivities. For the use of solar cells made of amorphous silicon, for example, pyrenes are suitable as indicators, while for crystalline silicon porphyrines and/or ruthenium complexes are good indicators.

Furthermore, the indicators can be advantageously immobilized on the solar cell. This can, for example, be accomplished by the deposition of the indicators with the aid of vapor deposition or sputtering processes or from a solution with subsequent vaporization of the solvent. A further advantageous possibility of immobilization consists in the doping of layer- or film-generating polymers with the indicators or the deposition of such doped layers or films on the solar cells. If the indicators are themselves a constituent of a polymer, then it is sufficient to deposit the sensitive polymer as a film or a layer on the solar cell.

Indicators, which selectively and reversibly change their spectral fluorescence or transmission under the influence of special gases or substances, can also be deposited on solar cells. This also causes the photoelectric current to change, the magnitude of which serves for the detection of gas or for verifying the presence of a substance.

Because spectrally wide-band sunlight or the radiation from artificial light fixtures is used as a measuring ray, it is of particular advantage and necessary for a still more efficient detection, to provide the indicators according to the invention additionally with fluorescent dyes or to cover them with them. For gas sensors such an additional fluorescent cover layer should be gas-permeable. The additionally used fluorescent dye molecules or fluorescent cover layers are chosen in such a manner, that their ranges of emissions coincide with the spectral absorption of the indicators. In this manner, the solar radiation or the artificial illuminating light is transformed and amplified into a spectrally narrowed measuring ray. Thus, for example, the UV-constituent of the sunlight can also be additionally transformed by the additional fluorescent substances into light in the visible range of the spectrum.

These additionally added fluorescent dyes or fluorescent layers continue to function simultaneously as filters, and by means of this filter effect they also support the sensor function of the sensors according to the invention.

The sensors according to the invention are, furthermore, even usable, when the substance, whose presence is to be verified qualitatively and quantitatively, is deposited on the solar cell during the measurement and its absorption properties are made use of. In this case as well, it is advantageous, to additionally deposit a fluorescent dye, so that the broad-band solar radiation, which is provided as a measuring ray, is spectrally narrowed. For example, following a calibration process, it is possible to verify the presence of oxygen, carbon dioxide or glucose in the blood by depositing 0.1 ml of blood on the solar cell sensor and measuring the photoelectric current, while at the same time adding fluorescent dyes, which displace the incident radiation toward a longer wave length and act as light filters. In the practical implementation of the measurement it is advantageous to place the blood to be investigated and the fluorescent dye at first in a polymer matrix, preferably on a cellulose basis, which is porous and capable of suction as well as transparent, and then to place it on the solar cell. According to the principle of the absorption measurement, the ozone concentration can also be determined by applying the sensors according to the invention, if one uses UV-sensitive solar cell materials and deposits fluorescent materials upon them, which amplify the measurement radiation to 340 nm.

It is advantageous, if the polymer materials or the polymeric indicator materials, which serve to immobilize the indicators, are gas-permeable, so that the verification of the presence of gases can also be carried out inside the polymer structure. For this, for example, silicones or polyhydroxyethylene-methacrylate are suitable. It is also advantageous, if the polymers are optically highly transparent, are good at forming a film and can be doped.

In summary it can be said, that by means of the sensors according to the invention a sensor is provided, which is cost-effective and mobile, which itself produces the electrical energy necessary to operate it, and which at the same time utilizes the sun light or artificial illuminating light as a measurement light ray.

In the following some examples of sensors or processes according to the invention for the detection of quantities to be measured or of substances will be described.

In order to prove the presence of ammonia, protonated styrylacridines are immobilized by red-emitting perylene-fluorescent dyes in a siloxane matrix and deposited on a solar cell consisting of mono-crystalline silicon. Protonated styrylacridines display a high degree of absorption in the spectral range between 600 and 800 nm, which almost disappears in the presence of ammonia (0–1000 ppm), because the dye is de-protonated and thus becomes colorless. By virtue of the existence of the red-emitting fluorescent dye, the short-wave portion of the solar radiation is transformed into red light and amplifies the spectral constituent of the radiation in the range of 600 to 800 nm, which is significant for the measurement. By means of this light amplification it is possible to verify the presence of even low concentrations of ammonia (<100 ppm) or to carry out the measurement with weak solar radiation, as, for example, on dark days or in interior spaces.

For the pH-value determination, chemo-sensitive acridines or fluorescent indicators such as, for example, fluoreszein, eosines, naphthaline derivatives, salicylic acid, quinine, Congo red, phenolphthaleines and others can be used, the spectral fluorescence and spectral transmission of which strongly changes when the pH-value varies. As a function of the indicators used, color changes of green-violet, colorless-blue, yellow-green or violet-colorless as well as changes in the fluorescence with strong effects on the photoelectric current occur, if the appropriate addition of solar cell material and the additionally added fluorescent dye for the spectral transformation of the solar radiation was made.

In order to determine the pH-value of blood, the dye phenol red is added to permeable polyacrylamide structures and deposited on the solar cell. As a function of the pH-value of the blood a color transformation of red-green occurs. In this case, a solar cell of amorphous silicon, the photoelectric current of which reacts most strongly during the occurring color change, is suitable.

For verifying the presence of $SO_2$, colorless organoplastic complexes, which assume an orange color after the adsorption of $SO_2$ are suitable. Here it is advantageous to add fluorescent dyes, which emit in the blue-green spectral range (for example coumarines and/or naphthalimides).

When fluorescent markers are used as metal indicators, a color change and an increase of the intensity of the fluorescence occur because of a formation of complexes. If one takes, for example, 4-nitro-7(1.4, 10-trioxa-7, 13-diaza-cyclopentadec-7-yl)-benzo [1, 2, 5] oxadiazol (NBO) as a marker of fluorescence, then this substance acts at first as a strong filter in the spectral range of 430 to 530 nm. In the presence of mercury ions ($Hg^2$) a fluorescent complex is formed with a high fluorescence intensity around 550 nm during excitation in the absorption range. Above 530 nm, thus, a strong light amplification occurs, which serves to produce a higher photoelectric current and thus to demonstrate the presence of metal ions.

The change in fluorescence in the case of biochemical processes, such as, for example, in the analysis of polymerase chain reactions (PCR), likewise produces a functional basis of the solar cell sensors according to the inventions. Here fluorescent reporter dyes, e.g. rhodamine-derivates, are used as fluorescence markers.

After the start of the polymerase chain reaction, the fluorescence extinction is canceled and the rhodamine-derivates emit strongly in the spectral range between 510 and 560 nm while affecting the electrical output magnitude of the solar cell. For the analysis of polymerase chain reactions, silicon solar cells are also suitable.

When verifying the presence of ozone, its strong oxidizing effect on the most diverse substances (e.g. metals, dyes) and the color changes associated with this, represent the operative principle. The oxidation of indigo into yellow isatine by ozone, for example, leads to changes in the spectral distribution of the radiation impinging upon the solar cells, if one uses indigo as a sensitive substance. The change of the photoelectric current is thus a measure for the ozone concentration present.

Figure 2:
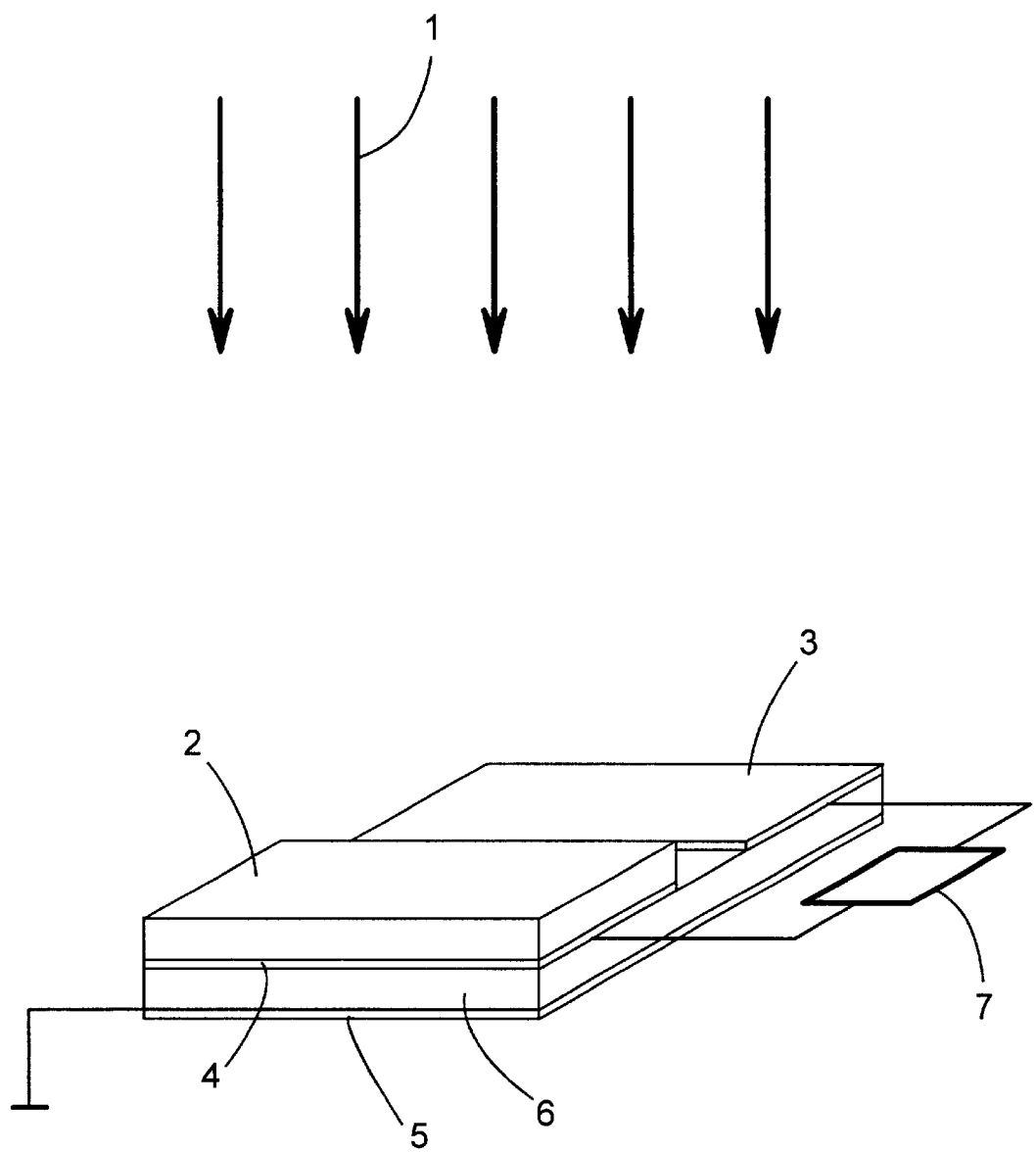
FIG. 2 is a perspective view of a sensor embodying the construction of the present invention.

FIG. 2 shows a sensor according to the invention. The sensor includes a solar cell 6, which carries electrodes 3, 4, 5 on its top and bottom surfaces. On its top surface, the electrodes 3 and 4 are positioned in such a manner that they are electrically separated from each other. On the electrode 4, there is a polymer layer 2 of siloxane or polyhydroxyethyl-methacrylate, which contains indicator molecules. The electrodes 3 and 4 are connected to an evaluation or indicator unit 7. According to FIG. 2, the solar radiation 1 reaches one of the active surface portions located on the electrode 4, which is coated with indicators and supplies the measurement signal. In addition, the solar radiation 1 gets to the reference plane, which includes the electrode 3 and which is either not coated or covered with a matrix material which was not doped. The active surface and the surface of reference are electrically separate from each other. As a result of this measure, a reference signal from electrode 3 is now available, which contains the variation of the radiation intensity and also the temperature dependence of the materials of the solar cells, and by means of which the changes can be compensated for. In this manner, measurements at different radiation intensities and ambient conditions are possible. The measurement signal and the reference signal from the electrodes 3 or 4 are carried to the evaluation and indicator unit 7, which then indicates the parameters to be detected. The evaluation and indicator unit 7, on the other hand, can be operated by the electric current generated by the solar cell 6.

The surface portions of the active surface and the reference surface are dimensioned in such a manner, that in conformance with the particular measuring task, a strong measurement signal is generated. Not shown is the possibility of depositing additional filter layers on the solar cells in order to improve the accuracy of the measurements.

In the following, three concrete examples of embodiments of the sensors according to the invention and the process according to the invention are shown.

EXAMPLE OF EMBODIMENT 1

For the aids test (HIV-Test) an optically transparent porous membrane is deposited on the reference portion as well as on the active portion of a poly-crystalline silicon solar cell. Subsequently, special gene-technically manipulated protein molecules are printed only upon the active measuring portion of the solar cell. Then one places a diluted drop of blood likewise on the active portion of the solar cell, which is followed by a tracing reagent. In the case of an HIV infection, a reaction takes place between the tracing reagent and the antibodies, which are present in the protein molecules, with a subsequent blue coloration. The blue coloration results in a change of the spectrum of the radiation impinging on the solar cells, as a result of which the photoelectric current increases.

From the increase of the photoelectric current it can be objectively concluded that an HIV effect is present.

EXAMPLE OF EMBODIMENT 2

In order to produce a temperature sensor, a solution $10^{-1}$ mole/L of the temperature-sensitive rhodamine B in the monomer hydroxyethyl-methacrylate (HEMA) with the addition of 0.1% azoisobutyronitrile (AIBN) is polymerized in the temperature range between 40 and 80 °C. The polymer is subsequently processed into a 5% solution in acetoacetalacid-ethylester (AEEE). With the use of a spray process, a portion of the surface of a solar element, which has an amorphous silicon base, is coated. The sensor element consists of two identical electrical units, whose signal relation is determined by a temperature-sensitive partial coating.

EXAMPLE OF EMBODIMENT 3

In order to show the presence of ammonia, 3% by weight of styryleacridines, which cause a strong increase of the transmission in the presence of ammonia in the spectral range of 600–800 nm, are added in solution to a siloxane polymer. To this doped polymer solution, a 1% by weight of the fluorescent dye perylene red RED 300 is added. In order to dissolve it better, the dye RED 300 is dissolved in chloroform and the dye solution of the doped polymer solution is added. The paint formulation produced in this manner is centrifuged with the use of a centrifuging process (1000 revolutions per minute) upon a mono-crystalline silicon solar cell. In this process, half of the active surface of the solar cell is covered. In this manner it is possible to generate a reference signal during the measurement.

During the measurement, the measurement signal originating from the sensitively coated solar cell portion is compared to the reference signal.

What is claimed is:

1. Process for the detection of a quantity to be measured, comprising providing a solar cell with at least a partial coating on at least one of its sides, wherein the coating comprises substances as indicators, the fluorescent behavior and/or the spectral transmission of which is a function of the quantities to be measured, and after the coating process or in connection with the coating process, exposing the solar cell to the quantity to be measured in the presence of natural or artificial light.

2. Process according to claim 1, wherein the indicators comprise thermotropic and/or thermochromic substances.

3. Process according to claim 1, wherein the solar cell is coated with a further fluorescent dye to serve as a light amplifier simultaneously with the indicators or as a cover coating on top of the indicators.

4. Process according to claim 1, comprising using a substance as a further fluorescent dye, which substance emits fluorescent light in a range of the spectrum in accordance with the absorption of the indicator.

5. Process according to claim 1, wherein the quantity to be measured is the presence and/or concentrations of gaseous, liquid or solid substances, and the gaseous, liquid and/or solid substance to be determined is used as an indicator.

6. Process according to claim 1, wherein the quantity to be measured is the presence of gaseous, liquid or solid substances in order to detect the physical or chemical parameters.

7. Process according to claim 6, wherein the quantity to be determined is the presence of oxygen, ammonia, sulphur dioxide, metals, or ozone, for determining the pH-value, pressure, temperature or humidity.

8. Process according to claim 7 wherein the quantity to be measured is in the area of medicine, biotechnology, environmental technology or measuring technology.

9. Process according to claim 7, wherein the quantity to be determined is the presence of mercury ions, for determining the pH-value, pressure, temperature or humidity.

10. Process according to claim 1, wherein the quantity to be measured is a physical or chemical parameter or the presence and/or concentrations of gaseous, liquid or solid substances.

11. Process according to claim 1, wherein the indicators comprise molecules.

12. Process according to claim 1, comprising measuring the fluorescent behavior and/or the spectral transmission of the quantity to be measured.

13. Sensor for a quantity to be measured, comprising a solar cell, which, on at least one of its sides, is at least partially provided with a coating, wherein the coating comprises substances as indicators, the fluorescent behavior and/or spectral transmission of which is a function of the quantity to be measured.

14. Sensor according to claim 13, wherein the coating has a polymer matrix, in which the indicators are imbedded.

15. Sensor according to claim 14, wherein the polymer matrix comprises siloxane, and/or polyhydroxy-ethylenemethacrylate.

16. Sensor according to claim 13, wherein the coating comprises thermotropic and/or thermochromic substances as indicators.

17. Sensor according to claim 13, wherein the coating comprises a further fluorescent dye as a light amplifier.

18. Sensor according to claim 13, wherein the coating is provided with a further cover layer, which contains a further fluorescent dye.

19. Sensor according to claim 18, wherein the cover layer is gas permeable.

20. Sensor according to claim 19, wherein the further fluorescent dye emits fluorescent light in a spectral range in accordance with the absorption of the indicator.

21. Sensor according to claim 20, wherein the indicators comprise porphyrines, chlorophyll, fluoresceins, rhodamines, ruthenium- and/or phthalocyanine complexes, pyrenes, polycyclic aromatics, rare earths and/or special fluorescent dyes, such as perylenes or pyronines.

22. Sensor according to claim 21, wherein the solar cell is based on amorphous or crystalline silicon, gallium arsenide compounds, indium phosphide compounds, germanium, selenium, cadmium-telluride, cadmium-sulfide, copper-indium-gallium-diselenide, copper-indium-sulfide, or mixed compounds of these elements.

23. Sensor according to claim 22, wherein only a part of the solar cell is coated and the coated region and the uncoated region each contain electrically separated electrodes.

24. Process for the manufacture of a sensor according to claim 13, wherein a coating material is deposited on a solar cell, where the coating material contains molecules or substances as indicators, or where to the coating material, after it is deposited, molecules and substances are added as indicators, whose fluorescent behavior and/or spectral transmission is a function of the quantities to be measured.

25. Process according to claim 24, wherein the coating material is deposited by vapor deposition or sputtering.

26. Process according to claim 25, wherein along with the coating material an additional fluorescent dye is deposited, or that a cover layer is deposited upon the deposited coating material, which cover layer contains an additional fluorescent dye.

27. Sensor according to claim 13 wherein the quantity to be determined is the presence of gaseous, liquid or solid substances in order to detect physical or chemical parameters.

28. Sensor according to claim 13, wherein the quantity to be measured is a physical or chemical parameter or the presence and/or concentrations of gaseous, liquid or solid substances.

29. Sensor according to claim 13, wherein the indicators comprise molecules.

* * * * *